US006300474B1

(12) United States Patent
Pestka

(10) Patent No.: US 6,300,474 B1
(45) **Date of Patent: *Oct. 9, 2001**

(54) MODIFIED INTERFERONS

(75) Inventor: Sidney Pestka, North Caldwell, NJ (US)

(73) Assignee: PBL Biomedical Laboratories, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/489,071

(22) Filed: Jun. 9, 1995

Related U.S. Application Data

(63) Continuation of application No. 08/257,784, filed on Jun. 10, 1994, now Pat. No. 5,789,551, which is a continuation-in-part of application No. 08/076,231, filed on Jun. 11, 1993, now abandoned.

(51) Int. Cl.[7] ........................ C07K 14/555; A61K 38/21; C12N 15/20; C12N 15/64

(52) U.S. Cl. ........................ 530/351; 424/85.4; 424/85.5; 424/85.6; 424/85.7; 514/2; 514/8; 514/12; 435/69.51; 435/71.2; 435/325; 435/252.3; 435/320.1; 435/471

(58) Field of Search ......................... 530/351; 424/85.14, 424/184.1, 198.1, 85.5, 85.6, 85.7; 514/2, 12, 8; 435/69.51, 172.3, 471, 71.1, 71.2, 325, 320.1, 252.3; 930/142

(56) References Cited

U.S. PATENT DOCUMENTS

| | | | |
|---|---|---|---|
| 3,699,222 | 10/1972 | Isaacs et al. | 424/85.4 |
| 4,683,195 | 7/1987 | Mullis et al. | 435/6 |
| 4,695,623 | 9/1987 | Stabinsky | 530/351 |
| 4,801,685 | 1/1989 | Goeddel et al. | 530/351 |
| 5,008,182 | 4/1991 | Sninsky et al. | 435/5 |
| 5,175,383 | 12/1992 | Leder et al. | 800/2 |
| 5,175,384 | 12/1992 | Krimpenfort et al. | 800/2 |
| 5,175,385 | 12/1992 | Wagner et al. | 800/2 |
| 5,372,808 | 12/1994 | Blatt et al. | 424/85.4 |
| 5,789,551 * | 8/1998 | Pestka | 530/351 |

OTHER PUBLICATIONS

Cunningham et al. (1989) Science, vol. 266, pp. 1081–1085.*
George et al. (1988) Macromolecular Sequencing & Synthesis Selected Methods & Applications, ch. 12, pp. 127–149, Alan R. Liss, Inc. N.Y.*
Mizoguchi et al. (1985) DNA, vol. 4, No. 3, pp. 221–232.*
Adolf, et al., "Natural Human Interferon–α2 is O–glycosylated", The Biochemical Journal, 276: 511–518 (1991).
Shuttleworth, et al., "Expression of Interferon–α and Interferon–β Genes in Human Lymphoblastoid (Namalwa) Cells", European Journal of Biochmeistry 133: 399–404 (1983).
Zoon, et al., "Purification and Caracterization of Multiple Components of Human Lymphoblastoid Interferonα*", The Journal of biological Chemistry, 267(21):15210–15216 (Jul. 25, 1992).
International Search Report.
Wang et al. (1994) J. Interferon Res. 14:41–6.
Emanuel et al. (1993) J. Biol. Chem. 268:12565–9.
Grander et al. (1992) Blood 79:2076–83.
Zoon et al. (1992) J. Biol. Chem. 267, No. 21:15210–6.
Desai et al. (1992) J. Interferon Res. 12:s138.
Antonelli et al. (1991) J. Infectious Dis. 163:882–5.
Colamonici et al. (1991) J. Interferon Res. 11:s54.
Diaz et al. (1991) J. Interferon Res. 11:s85.
Adolf et al. (1991) Biochem. 276:511–8.
Moormeier et al. (1989) Leukemia and Lymphoma 1:43–5.
Freund et al. (1989) British J. Haematology 72:350–6.
Steis et al. (1988) New Eng. J. Med. 318:1409–13.
Hotta et al. (1988) J. Interferon Res. 8:51–60.
Itri et al. (1987) Cancer 59:668–74.
Von Wussow et al. (1987) J. Interferon Res. 7:680.
Pestka et al. (1987) Ann. Rev. Biochem. 56:727–77.
Pestka, S.(1986) Methods in Enzymology 119:3–23.
Hotta et al. (1986) Methods in Enzymology 119:481–5.
Foon et al. (1986) American J. Med. 80:351–6.
Huber et al. (1985) Oncology 42,suppl. 1:7–9.
Henco et al. (1985) J. Mol. Biol. 185:227–60.
Quesada et al. (1985) J. Clinical Oncology 3:1522–8.
Langer et al. (1984) J. Investigative Dermatology 83:128s–36s.
Pestka, S. (1983) Arch. Biochem. Biophys. 221:1–37.
Rehberg et al. (1982) J. Biol. Chem. 257:11497–502.
Hobbs et al. (1982) J. Biol. Chem. 257:4071–6.
Pestka et al. (1981) Methods in Enzymology (S. Pestka,ed.) 78:3–14.
Staehelin et al. (1981) J. Biol. Chem. 256:9750–4.
Rubinstein et al. (1981) Arch. Biochem. Biophys. 210:307–18.
Streuli et al. (1980) Science 209:1343–7.
Goeddel et al (1980) Nature 287:411–6.
Koeffler et al. (1978) Science 200:1153–4.

* cited by examiner

*Primary Examiner*—Prema Mertz
(74) *Attorney, Agent, or Firm*—Ropes & Gray

(57) ABSTRACT

A new class of polypeptides is disclosed, along with a method for identifying and producing such polypeptides, having the characteristic of being unique to diseased states, particularly tumors and blood-borne malignancies. These new polypeptides are active and will be useful for therapeutic purposes.

11 Claims, 5 Drawing Sheets

```
                                                             ATGGCCTTG       9
                                                             MetAlaLeu
                                                             -23
10     TCCTTTTCTTTACTGATGGTCGTGCTGGTACTCAGCTACAAATCCATCTGCTCTCTGGGC   69
       SerPheSerLeuLeuMetValValLeuValLeuSerTyrLysSerIleCysSerLeuGly
       -20                          -10                            -1

70     TGTGATCTGCCTCAGACCCACAGCCTGCGTAATAGGAGGGCCTTGATACTCCTGGCACAA   129
       CysAspLeuProGlnThrHisSerLeuArgAsnArgArgAlaLeuIleLeuLeuAlaGln
        1                          10                            20

130    ATGGGAAGAATCTCTCCTTTCTCCTGCTTGAAGGACAGACATGAATTCAGATTCCCAGAG   189
       MetGlyArgIleSerProPheSerCysLeuLysAspArgHisGluPheArgPheProGlu
                                   30                            40

190    GAGGAGTTTGATGGCCACCAGTTCCAGAAGACTCAAGCCATCTCTGTCCTCCATGAGATG   249
       GluGluPheAspGlyHisGlnPheGlnLysThrGlnAlaIleSerValLeuHisGluMet
                                   50                            60

250    ATCCAGCAGACCTTCAATCTCTTCAGCACAGAGGACTCATCTGCTGCTTGGGAACAGAGC   309
       IleGlnGlnThrPheAsnLeuPheSerThrGluAspSerSerAlaAlaTrpGluGlnSer
                                   70                            80
```

FIG. 1A

```
310  CTCCTAGAAAAATTTTCCACTGAACTTTACCAGCAACTGAATGACCTGGAAGCATGTGTG  369
     LeuLeuGluLysPheSerThrGluLeuTyrGlnGlnLeuAsnAspLeuGluAlaCysVal
                                   90                           100

370  ATACAGGAGGTTGGGGTGGAAGAGACTCCCCTGATGAATGAGGACTCCATCCTGGCTGTG  429
     IleGlnGluValGlyValGluGluThrProLeuMetAsnGluAspSerIleLeuAlaVal
                                  110                           120

430  AGGAAATACTTCCAAAGAATCACTCTTTATCTAACAGAGAAGAAATACAGCCCTTGTGCC  489
     ArgLysTyrPheGlnArgIleThrLeuTyrLeuThrGluLysLysTyrSerProCysAla
                                  130                           140

490  TGGGAGGTTGTCAGAGCAGAAATCATGAGATCCCTCTCGTTTTCAACAAACTTGCAAAAA  549
     TrpGluValValArgAlaGluIleMetArgSerLeuSerPheSerThrAsnLeuGlnLys
                                  150                           160

550  AGATTAAGGAGGAAGGATTGA  570
     ArgLeuArgArgLysAspEnd  166
```

FIG. 1B

```
                                .         .         .         .         .
  1 MALSFSLLMVVLVLSYKSICSLGCDLPQTHSLRNRRALILLAQMGRISPF  50
    || |||||||||||||||||||||||||||||||||||||||||||||||
  1 MARSFSLLMVVLVLSYKSICSLGCDLPQTHSLRNRRALILLAQMGRISPF  50
                                .         .         .         .         .
 51 SCLKDRHEFRFPEEEFDGHQFQKTQAISVLHEMIQQTFNLFSTEDSSAAW 100
    ||||||||||||||||||||||||||||||||||||||||||||||||||
 51 SCLKDRHEFRFPEEEFDGHQFQKTQAISVLHEMIQQTFNLFSTEDSSAAW 100
                                .         .         .         .         .
101 EQSLLEKFSTELYQQLNDLEACVIQEVGVEETPLMNEDSILAVRKYFQRI 150
    |||||||||||||||||||||||||||||||||| |||||||||||||||
101 EQSLLEKFSTELYQQLNDLEACVIQEVGVEETPLMNEDFILAVRKYFQRI 150
                                .         .         .
151 TLYLTEKKYSPCAWEVVRAEIMRSLSFSTNLQKRLRRKD 189
    |||| |||||||||||||||||||:||||||.| |||||
151 TLYLMEKKYSPCAWEVVRAEIMRSFSFSTNLKKGLRRKD 189
```

FIG. 2

MODIFIED INTERFERONS

CROSS REFERENCE TO RELATED APPLICATION

This application is a Continuation of application Ser. No. 08/257,784 filed Jun. 10, 1994, now U.S. Pat. No. 5,789,551, which is a continuation in part of U.S. application Ser. No. 08/076,231, filed Jun. 11, 1993 now abandoned.

FIELD OF THE INVENTION

This invention relates to the field of biotechnology and more particularly to polypeptides having antitumor, antiviral, immunomodulatory and other activities, DNA that codes for such polypeptides, recombinant vectors that include such DNA host organisms transformed with the recombinant vector that produces the polypeptide and therapeutic application of the polypeptide.

The publications and other materials hereof used to illuminate the background of the invention, and in particular cases, to provide additional details respecting its practice are hereby incorporated by reference, and for convenience are numerically referenced by the following text and respectively grouped in the appended bibliography.

BACKGROUND OF THE INVENTION

Human leukocyte interferon was first discovered and prepared in the form of very crude fractions by Isaacs and Lindenmann (1, 2). Efforts to purify and characterize the material have led to the preparation of relatively homogeneous leukocyte interferons derived from normal or leukemic (chronic myelogenous leukemia or "CML") donors leukocytes These interferons are a family of proteins characterized by a potent ability to confer a virus-resistant state in their target cells. In addition, interferon can inhibit cell proliferation, modulate immune responses and alter expression of proteins. These properties have prompted the clinical use of leukocyte interferon as a therapeutic agent for the treatment of viral infections and malignancies.

With the advent of recombinant DNA technology, the controlled microbial production of an enormous variety of useful polypeptides has become possible. The workhorse of recombinant DNA technology is the plasmid, a non-chromosomal circle of double-stranded DNA found in bacteria and other microbes, oftentimes in multiple copies per cell. Included in the information encoded in the plasmid DNA is that required to reproduce the plasmid (i.e., an origin of replication) and ordinarily, one or more selection characteristics such as, in the case of bacteria, resistance to antibiotics which permit clones of the host cell containing the plasmid of interest to be recognized and preferentially grown in selective media. The utility of plasmids lies in the fact that they can be specifically cleaved by one or another restriction endonuclease or "restriction enzyme," each of which recognizes a specific site in the DNA. Heterologous genes or gene fragments may be inserted into the plasmid at the cleavage site. To construct vectors with specific sequences inserted, DNA recombination is performed outside the cell, but the resulting "recombinant" plasmid can be introduced into cells by a process known as transformation and large quantities of the heterologous gene-containing recombinant plasmid obtained by growing the transformant. Moreover, where a promoter which governs the transcription of the encoded DNA message, is properly placed upstream (5') of a coding sequence or a gene, the resulting expression vector can be used to produce the polypeptide sequence for which the inserted sequence or gene codes, a process referred to as expression.

Expression is initiated in a region known as the promoter which is recognized by and bound by RNA polymerase. In many cases promoter regions are overlapped by "control" regions such as the bacterial operators. Operators are DNA sequences which are recognized by so-called repressor proteins which serve to regulate the frequency of transcription initiation at a particular promoter. The polymerase travels along the DNA, transcribing the information contained in the coding strand from its 5' to 3' end into messenger RNA (mRNA) which is in turn translated into a polypeptide having the amino acid sequence for which the DNA codes. Each amino acid is encoded by a nucleotide triplet or "codon" within the coding sequence, i.e., that part which encodes the amino acid sequence of the expressed product. In bacteria (e.g. *Escherichia coli*) the mRNA contains a ribosome binding site, a translation initiation or "start" signal (ordinarily ATG in the DNA, which in the resulting mRNA becomes AUG), the nucleotide codons within the coding sequence itself, one or more stop codons, and an additional sequence of messenger RNA, the 3' untranslated region. Ribosomes bind to the binding site provided on the messenger RNA, in bacteria ordinarily as the mRNA is formed, and produce the encoded polypeptide, beginning at the translation start signal and ending at the stop signal. The desired product is produced if the sequences encoding the ribosome binding site are positioned properly with respect to the AUG initiator codon and if all remaining codons follow the initiator codon in phase. The resulting product may be obtained from the host cell and recovered by appropriate purification. In other systems, proteins may be secreted from the host cells. A wide variety of expression vectors and host systems exist so that RNA and proteins may be expressed in prokaryotic and eukaryotic cells as well as in intact animals and plants.

During the past several decades a large number of human and animal interferons have been produced, identified, purified and cloned (see ref. 1–72). Several of the interferon preparations have been prepared for clinical trial in both crude form, for some of the original interferon preparations, as well as in purified form. Several individual recombinant interferon-α species have been cloned and expressed. The proteins have then been purified by various procedures and formulated for clinical use in a variety of formulations (73). Most of the interferons in clinical use that have been approved by various regulatory agencies throughout the world are mixtures or individual species of human α interferon (Hu-IFN-α). In some countries Hu-IFN-β and γ have also been approved for clinical trial and in some cases approved for therapeutic use (56,74). The major thesis underlying clinical use of these interferons was that they were natural molecules produced by normal individuals. Indeed, the specific thesis was that all the interferons prepared for clinical use, be they natural- or recombinant-generated products, represented interferons that were produced naturally by normal people. This is true for a large number of interferons as well as specific growth factors. lymphokines, cytokines, hormones, clotting factors and other proteins that have been produced (17, 21, 22, 25–27, 29–34, 39, 40, 45–51, 53–57, 62–64, 68–72).

Reports have suggested that Hu-IFN-αA (also designated Hu-IFN-α2a and by the trade name Roferon A) was not represented in interferons produced by a normal population of individuals (75–79). Believing that certain interferons (or, more generically, certain polypeptides) are uniquely found in diseased cells, the inventor of the present invention undertook to identify interferons which are so uniquely characterized. For convenience the inventor began by screening known interferons, in particular, the sources of the several variants of Hu-IFN-α2 that have been described. As discussed more fully below, it was found that the source of two of the variants of Hu-IFN-α2, Hu-IFN-α2a and Hu-IFN-α2c, are not present in normal individuals. Only Hu-IFN-α2b is found in normal individuals (79).

DESCRIPTION OF THE DRAWINGS

FIG. 1. Nucleotide and Amino Acid Sequence of Hu-IFN-α001 (SEQ ID NOS: 1 and 2). The location of the AlwNI site is underlined. The signal peptide is shown as the 23 amino acids labeled −1 to −23.

FIG. 2. Comparison of the Protein Sequence of Hu-IFN-α001 (SEQ ID NO: 2)with that of Hu-IFN-αJ (SEQ ID NO: 3). The signal peptide represents the first 23 amino acids at the amino terminus.

SUMMARY OF INVENTION

Figure 3:
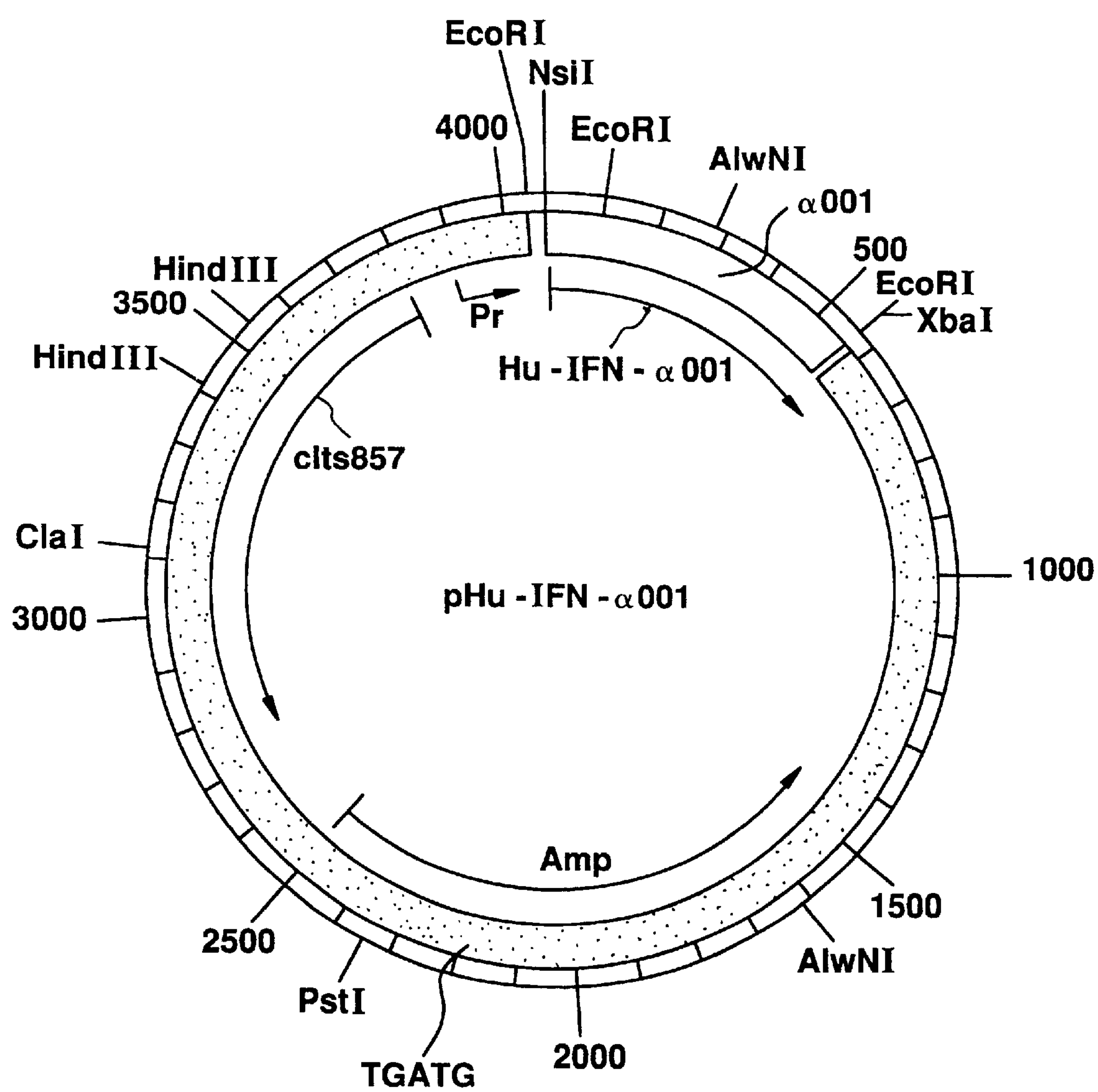
FIG. 3. Expression vector for Hu-IFN-α001. The structure of the plasmid pHu-IFN-α001 is shown. The NsiI site represents nucleotide position #1. The $P_R$ promoter drives expression of Hu-IFN-α001.

An extensive analysis of normal individuals from various ethnic and racial backgrounds as well as two tumor cell lines has shown that certain interferons originated from two cell lines that were obtained from patients with disease, in particular, malignancies of the hemopoietic system (79). These results lead the inventor to conclude that there is a new class of interferon molecules which are present in diseased states, specifically in tumors and blood borne malignancies. This discovery of a new class of interferons provides a wide variety of potentially new interferons for clinical and therapeutic use. These interferons include not only Hu-IFN-α species, but also Hu-IFN-β, Hu-IFN-γ and Hu-IFN-ω, as well as other newly described interferons in other animals and species. The observations suggest that group factors, cytokines, lymphokines, clotting factors, peptide and polypeptide hormones, adhesion factors and many other molecules are also modified in disease processes. Therefore, modified forms of all these cytokines, lymphokines, growth factors, adhesion molecules, enzymes, clotting factors, peptide and polypeptide hormones, etc. will also occur in tumors and other diseases. Based on two presently identified members of this class (not previously recognized as such), these interferons are active, are as active as the standard molecules, and in fact have been used effectively for therapeutic purposes. A paper co-authored by the inventor and listed hereafter as Reference No. 79 is particularly related to the invention and is incorporated herein by reference insofar as may be needed for a full understanding of the invention. That paper is more fully described, and is furnished as an attachment to a contemporaneously filed Information Disclosure Statement.

DETAILED DESCRIPTION OF THE INVENTION

Four distinct classes of interferons (IFNs) are known to exist in humans. The IFN-α family represents the predominant class of IFNs and are produced by stimulated peripheral blood leukocytes (10 –15, 17–27, 29, 50, 51, 57–59, 61, 63, 64, 68, 70), and lymphoblastoid and myeloblastoid cell lines (28, 30, 60). Cloning of the IFN-α genes from these cells has revealed that IFN-α is encoded by a multigene family consisting of about 15 functional genes and four pseudogenes (17, 26, 27, 29, 31, 50, 51, 53, 54, 57, 61, 63, 64, 65). U.S. Pat. No. 4,801,685 by Goeddel, D. V., and Pestka, S., states "the hybridizations were performed at 15° C. for 14 hours in 6×SSC, 10X Denhardt's solution, as described by Wallace et al. (28). Filters were washed for 5' (3 times) at 0°C. in 6×SSC, dried, and exposed to x-ray film." It has been uncertain whether or not some of the cloned human IFN-α genes and cDNAs with few nucleotide differences, such as the Hu-IFN-αA, Hu-IFNc-α2 and Hu-IFN-α2(Arg) genes, are allelic variants or represent distinct genes.

To determine if these sequences do indeed represent separate genes or are instead polymorphic variants of a single gene, sequences representing only the Hu-IFN-αA, Hu-IFN-α2 and Hu-IFN-α2(Arg) genes were amplified by nested polymerase chain reaction (PCR) from human genomic DNAs of healthy consenting individuals. These sequences were then subcloned and examined by sequencing of individual clones. In addition, the DNAs were examined from KG-1 (80) and Namalwa (81) cell lines from which the Hu-IFN-αA and Hu-IFN-α2(Arg) cDNAs, respectively, were cloned.

MODES FOR CARRYING OUT INVENTION

Three oligodeoxynucleotides were prepared by the phosphoramidite method (82, 83) and purified (84). Primer I (5'-TGGGCTGTGATCTGCCTC-3')(SEQ ID NO: 4) complementary to nucleotides 125 to 142 at the 5' end was used with Primer II (5'-CATGATTTCTGCTCTGACAACC-3')(SEQ ID NO: 5) complementary to nucleotides 552 to 573 at the 3' end to amplify the desired nucleotide sequences. The DNA, as amplified by the polymerase chain reaction (PCR) with this primer pair, was expected to represent sequences from most of the IFN-α gene family (79). This conserved PCR product was then used as template in a second amplification reaction with the same 3' oligonucleotide but with a 5' oligonucleotide specific for the human IFN-αA. IFN-α2 and IFN-α2(Arg) genes only (79). The second reaction produced a product of 430 bp when Primer III (5'-AACCCACAGCCTGGGTAG-3')(SEQ ID NO: 6) complementary to nucleotides 144 to 161 was substituted for the Primer I. The 430 bp DNA was purified and cloned into the SmaI site of pBluescript-SK$^-$ (Stratagene, LaJolla, Calif.) as described (79, 85, 86).

DNA of the plasmids was prepared by the alkaline lysis miniprep procedure (86, 87) from 1 ml cultures grown overnight in LB medium containing 100 μg/ml ampicillin. The resultant DNA pellet was sequenced by the dideoxy chain termination procedure (79, 88, 89). The reactions were run on 6% polyacrylamide gels which were then dried and exposed to X-ray film overnight at room temperature with an intensifying screen.

Reverse transcriptase PCR (RT-PCR) was used to analyze the expression of the IFN-α subtypes αA, α2 and α2(Arg) in the KG-1 and Namalwa cell lines (90). RNA was isolated at 6 hours after induction from Sendai virus-induced KG-1 cells (60) and at 8 hours post induction from NDV-stimulated Namalwa cells (91, 92).

DNA was extracted from the human myeloblastoid cell line KG-1 and from the lymphoblastoid Namalwa cell line by a modification of the method of Pellicer et al. (93). After obtaining informed consent, human genomic DNA was prepared from whole blood samples collected from normal, healthy individuals by ammonium acetate precipitation as described (79, 94).

METHODOLOGICAL BASIS FOR INVENTION

The DNA from 11 normal individuals was amplified by nested PCR then cloned and sequenced as described above. The number of sequences corresponding to the various human IFN-α species is shown in Table 1. It can be seen that neither the sequence for the αA gene nor the α2(Arg) gene was detected in any of the normal individuals examined in this study. As shown in Table 2, however, the αA sequence was detected in the DNA from the KG-1 cell line, but not in Namalwa cells; and the α2(Arg) sequence was detected in the DNA from the Namalwa cell line, but not in KG-1 cells.

TABLE I

Frequency of Hu-IFN-αA, -α2 and α2(Arg) Clones From Normal Individuals

| Interferon Variant | Number of Clones |
|---|---|
| IFN-α2 | 165 |
| IFN-αA | 0 |
| IFN-α2(Arg) | 0 |
| Other[1] | 36 |
| Total | 201 |

[1]Other refers to sequences which contained one or more mutations in an area unrelated to the αA and α2(Arg) specific differences. It should be noted that the frequency of mutations detected is in the range or slightly lower than that predicted from the combined error rates of Taq DNA polymerase and Sequenase DNA polymerase (95, 96). Previous analysis of IFN-α2 genes have been reported (97, 98), but did not discern any differences in their representation in the DNA from normal individuals. Descriptions and abbreviations relevant to interferon are described in detail in several references (10–12, 61, 99, 100).

TABLE 2

Frequency of IFN-α Clones From KG-1 and Namalwa Cell Lines

| Cells | IFN-α2 | IFN-αA | IFN-α2(Arg) | Other | Total |
|---|---|---|---|---|---|
| KG-1 cells | 15 | 10 | 0 | 16 | 41 |
| Namalwa cells | 22 | 0 | 13 | 2 | 37 |

Restriction endonuclease analysis to detect the IFN-α A gene was also performed on DNA from five of the individuals from whom clones had been sequenced and on DNA from seven additional people that were not examined by DNA sequencing. It was found that the restriction endonuclease analysis of the amplified DNA from all of these individuals showed no IFN-αA gene present (See Ref. 79, FIG. 2).

PREFERRED EMBODIMENT OF INVENTION

From the foregoing analysis, it can be concluded that in human DNA from a wide variety of humans only Hu-IFN-α2 is present. The species Hu-IFN-αA and Hu-IFN-α2 (Arg), not present in the DNA of 11 normal individuals, apparently arose during the development of the disease and/or the establishment of the cell lines in culture. It is noteworthy that the expression of these alleles of Hu-IFN-α2 yields IFN-α species with high activity in a wide variety of assays (63, 68, 69, 101–115). The specific activities of all three of these IFN-α species are comparable. Furthermore, it has been reported that patients treated with Hu-IFN-αA produced a higher level of anti-interferon antibodies than patients treated with Hu-IFN-α2 or Hu-IFN-αn (Welferon: a preparation of mixed Hu-IFN-α species produced by induced Namalwa cells) (116–124). Some of the new interferons produced by the described invention may be able to by-pass neutralization by the antibodies produced in patients treated with IFN-α preparations in current use. Such new IFN-α species should be able to be used to treat patients who have relapsed because of neutralization of the administered IFN-α species.

While the inventor has, for convenience, used Hu-IFN-α2 and its known variants for establishing his hypothesis of the existence of a class of super or tumor interferons, it will be apparent to those skilled in the art that the results extend to an entire class of such interferons, as well as other polypeptides. Illustrative of this conclusion is the extraordinary high percentage of variant forms of the IFN-α2 and αA genes in KG-1 cells—i.e., 39% (16/41), much more than could be explained by experimental error, as shown in the column labeled "Other" of Table 2.

It will also be apparent that the method of the invention, as illustrated above for Hu-IFN-α2, can be applied to any protein. In the general case, a primer pair is chosen to encompass part or all of the nucleotide coding sequence with the use of DNA from tumor cells or from cultured cells as templates for the PCR. The PCR product is then cloned and sequenced. The amino acid sequence predicted by the nucleotide sequence so obtained is compared to the sequence of the protein in normal individuals. Proteins with amino acid sequences different from those proteins in normal individuals are then cloned in appropriate expression vectors (11, 12, 14, 17, 45, 53, 54, 57, 63, 69, 86, 103), produced, purified and characterized. Those with desirable activities are then developed for therapeutic use.

The origin of the tumor interferons or super interferons is unknown. Yet, it is clear that they are developed during the pathological process. It is believed that the cells producing these interferons have been selected during development and progress of the disease.

The presence of allelic forms of IFN-α2 in the KG-1 and Namalwa cells is most noteworthy. DNA from leukocytes from normal individuals did not contain these variants. Because both the KG-1 and Namalwa cells originated from patients with leukemia or lymphoma, it is believed that this alteration is an early change in progression of these diseases. Indeed, it has been reported that there are significant gross changes in restriction endonuclease digestion patterns for the IFN-α genes in acute leukemias (125, 126).

The disease mechanisms involved in developing malignant cells and selection of those cells produce a wide variety of genetic changes in the resultant tumor cells. In order for cancer cells to grow unfettered, to escape the normal controls and to metastasize, the usual regulatory network of the immune system, involving growth inhibitors as the interferons and growth factors and hormones, may be modified. The control of cell growth and nonmalignant behavior is a delicate balance of many regulatory factors, a few of which gone astray can alter the normal growth patterns. Although it has been reported that changes in the DNA of cancer cells occurs, the changes have been focussed on oncogenes and tumor suppressor genes that lead to the malignant phenotype. The inventor has provided data that the changes are more pervasive than expected, not merely those changes focussed on oncogenes and tumor suppressors. Furthermore, by genetic changes (mutations in DNA) and selection of tumor cells for aggressiveness, many alterations will be embodied in the final tumor cell population. The new proteins produced will have lower, the same or higher activities than the normal proteins. By identifying those modified proteins associated with changes in activity, it will be possible to identify those proteins with new and/or enhanced activities.

From an analysis of initial clones obtained from the KG1 cell line (53, 54, 63), it was shown that several abnormal interferons exist in this cell line (also see ref. 61 for list of IFN-α species). This is especially evident in that αB (not previously recognized as an abnormal interferon) has an insertion and compensating deletion making an abnormal protein that differs from Hu-IFN-α8, the normal counterpart. The presence of an insertion and a compensating deletion producing a normal sized molecule suggests some enormous selective pressures to produce these interferons. The fact that an insertion and a deletion would be incorporated into a molecule simply by random stochastic processes without external pressures is highly unlikely. Thus, these modified interferons are seen to represent an entire new family of molecules that have been developed under the pressure of enormous external forces to provide for the selection of these species.

With respect to the interferons produced by mechanisms to enhance or combat the disease process, some may indeed have unusual properties and may be more active than some of the interferons produced by normal cells. For example, since interferon is a growth inhibitory molecule, production of a new interferon that could down regulate the receptors for interferon in cells and help select for cells without interferon receptors or low levels of interferon receptors may enhance the disease process. Such interferons could also help select cells with an altered signal transduction mechanism, but normal receptor number. Thus, a cell producing spontaneously some interferon, could be expected to have initially a low level of receptors due to down regulation and its growth would likely be reduced. Nevertheless, during the multiplication of such cells, cells would be selected that would have low levels of receptors so that they could escape the inhibition of the endogenous interferon. The same would hold for a wide variety of other molecules such as cytokines, lymphokines, tumor suppressors, growth factors, anti-growth factors, matrix molecules, hormones, angiogenic factors, clotting factors, etc., all molecules that can control growth and/or metastases in one manner or another.

The altered proteins described herein are found in tumor cells or cultured cells obtained from tumors. Furthermore, selection of cell-lines in culture can also produce some of the alterations as selection in vivo.

CLONING OF Hu-IFN-α001

A new interferon was amplified from the genomic DNA of KG-1 cells (ATCC CCL 246) based on the strategies outlined hereinbefore and by the procedures described herein and elsewhere (79). The primers used to amplify the genes are shown in Table 3. The 5' primer contains an ApaI site, and the 3' primer contains an XbaI site for cloning. The PCR reactions were carried out in 50 μl with 100 ng KG-1 template DNA, 100 ng of each primer (6431 and 6432), 0.2 mM of each dNTP, and 2.5 units of Taq DNA Polymerase for 30 cycles of 94° C. 30 seconds. 50° C. 30 seconds. 72° C. 30 seconds in the Perkin Elmer model 9600 thermocycler. Products of the PCR amplification were cloned into the ApaI and XbaI sites of plasmid pBluescript II KS+ (Stratagene) and then transformed into competent *E. coli* strain DH5α cells. Competent cells were prepared in 12% PEG and 36% glycerol in Luria-Bertani medium (L-broth medium, 10 g tryptone, 5 g yeast extract, 10 g NaCl, pH 7.3) from Digene (Silver Spring, Md. 20904, Cat. No. 3500-1002) as described (127). Plasmid DNA was isolated from 2.0 ml of overnight cultures grown at 37° C. by a modified alkaline lysis procedure as reported (128). The size of the inserts was determined by digestion with restriction endonucleases KpnI and SacI that flanked the cloning sites in the vector pBluescript. A total of 10 independent colonies were identified that contained a 700 base pair insert.

TABLE 3

Primers for PCR Amplification

| Primer | Sequence | Length | Primer No. |
|---|---|---|---|
| 5' | GCGGGCCCCAATGGCCYTGYCCTTT (SEQ ID NO: 7) | 25 | 6431 |
| 3' | GCTCTAGAAYTCATGAAAGYGTGA (SEQ ID NO: 8) | 24 | 6432 |

The DNA from one of the clones (plasmid pBS001) was sequenced in both directions. Automated DNA sequencing was performed on a Genesis 2000 Automated DNA Sequencer (DuPont, Wilmington, De.) with the primers shown in Table 4 by methods previously reported (86, 88, 89). All sequences were performed on both strands. Automated sequencing was carried out and the results were compiled to create a consensus sequence. The sequence determined from the T3 primer represents the 5' end of the insert, the T7- derived sequence represents the 3' end.

The sequence so determined is designated Hu-IFN-α001 and is shown in FIG. 1 (SEQ ID NO: 1). The location of the AlwNI restriction endonuclease recognition site (5' CAGNNNCTG 3') (SEQ ID NO: 9)that was used for the splicing of the Hu-IFN-α001 insert into the expression vector TGATG (129) is indicated in the figure by underlining. The signal peptide is shown as the 23 amino acids labeled −1 to −23. As seen in FIG. 1 (SEQ ID NO: 2), the mature protein contains 166 amino acids.

TABLE 4

Primers used for Sequencing

| Designation | Sequence | Primer No. | Position in Hu-IFN-α001 | Direction |
|---|---|---|---|---|
| IFN-A1 | CTTGAAGGACAGACATG (SEQ ID NO: 10) | 6942 | 157–172 | F |
| IFN-A2 | CTGTCCTCCATGAGATG (SEQ ID NO: 11) | 6941 | 233–249 | F |
| IFN-A3 | GGTCATTCAGCTGCTGG (SEQ ID NO: 12) | 6940 | 339–355 | R |
| IFN-A4 | TCCTCCTTCATCAGGGG (SEQ ID NO: 13) | 6939 | 397–413 | R |
| T3 | ATTAACCCTCACTAAAGA (SEQ ID NO: 14) | 13 | Vector | F |
| T7 | TAATACGACTCACTATA (SEQ ID NO: 15) | 17 | Vector | R |

All primers are shown from 5' to 3' orientation. The column designated "Direction" represents the direction of sequencing with respect to the sequence of the Hu-IFN-α: "F" represents forward: "R" - reverse. Oligodeoxynucleotides were synthesized on an Applied Biosystem DNA synthesizer model 380B by the phosphoramidite method (83, 130).

A comparison of the protein sequence with other human interferon alpha species (Hu-IFN-α)(SEQ ID NO: 2) demonstrates that Hu-IFN-α001 is most closely related to Hu-IFN-αJ (SEQ ID NO: 3). That comparison is graphically depicted in FIG. 2. A summary of the known Hu-IFN-α sequences has been previously reported (61). There are a total of six amino acid changes compared to Hu-IFN-αJ. The data clearly demonstrate that this tumor derived Hu-IFN-α species is different from any other known Hu-IFN-α species previously reported. Furthermore, it would not have been possible to predict this specific sequence as the number of possible proteins with alterations in these six positions is $20^6$ or 64,000,000. One of the amino acid changes is in the signal peptide sequence; the remaining five alternations are in the mature protein. It is also to be emphasized that the derived Hu-IFN-α species presented here is a natural interferon derived from tumor cells. It is not a synthetic construct prepared by simile pit six positions.

Expression of the Hu-IFN-α001 gene was accomplished in two steps. The plasmid pBS001 was digested with restriction endonuclease KpnI (5' end of Hu-IFN-α001 sequence). The KpnI ends were made blunt by incubation with T4 DNA polymerase in the following reaction mixture: 1 μg of DNA; 33 mM Tris acetate, pH 7.9; 66 mM potassium acetate; 10 mM magnesium acetate; 0.5 mM dithiothreitol: 100 μg/ml BSA (bovine serum albumin); 2 ml of each of the four dNTPs; 5 units of T4 DNA polymerase (United States Biochemical Corp.); total volume of 18 μl. Incubation was performed for 5 minutes at 37° C. to prepare the blunt ends. The plasmid DNA was then digested with XbaI (3' end of Hu-IFN-α001 sequence) to release the insert containing the Hu-IFN-α001 sequence. The DNA fragments were then purified as described (86). The TGATG vector was prepared by digestion with restriction endonuclease SacI, followed by preparing blunt ends with T4 DNA polymerase as described above, and then digested with restriction endonuclease XbaI. The fragment containing the Hu-IFN-α001 insert was then ligated to the pTGATG expression vector (129). After ligation the DNA was transformed into competent *E. coli* DH5α cells. Colonies were analyzed by growing the cells as described above to isolate plasmid DNA. The plasmids were then digested with restriction endonucleases EcoRI and XbaI to determine the size of the insert An expression vector for Hu-IFN-αJ was prepared as previously described for the expression plasmids for Hu-IFN-αB2 and Hu-IFN-αA/D (131).

The nucleotide sequences encoding Hu-IFN-αJ and Hu-IFN-α001 contain an AlwNI site in identical positions of the sequence (FIG. 3); and, as illustrated in FIG. 3, which shows the structure of the plasmid pHu-IFN-α001 containing the expression vector for Hu-IFN-α001 there is a second AlwNI site in the vector itself.

In addition, because the AlwNI recognition sites (CAGNNN^CTG)(SEQ ID NO: 9) have three unspecified nucleotides (NNN) in the 3' overhang, the religations are specific and asymmetric. Accordingly, pTGATG vectors (129) encoding Hu-IFN-αJ and Hu-IFN-α001 were digested with restriction endonuclease AlwNI to isolate the large vector and Hu-IFN-α001 (3' end) fragments, respectively. The Hu-IFN-α001 fragment was then ligated into the vector fragment from plasmid pHu-IFN-αJ to yield the *E. coli* expression vector pHu-IFN-α001, as shown in FIG. 3, which was transfected into competent *E. coli* (DH5α) cells (86).

Plasmid pHu-IFN-α001 is deposited with the American Type Culture Collection (ATCC) at 12301 Parklawn Drive, Rockville, Md. 20852; Accession number: 69640; Deposit date Jun. 7, 1994; and designated as plasmid pHu-IFN-α001 (*E. coli* DH5α/pHu-IFN-α001 as the host vector system).

The *E. coli* (DH5α) cells containing the expression vector pHu-IFN-α001 were grown in 875 ml of Medium A overnight at 30° C. in one 2 liter flask with rotary shaking. Medium A consists of $KH_2PO_4$ (4.5 g/L), $Na_2HPO_4 \cdot 7H_2$) (0.369 g/l), thiamine hydrochloride (0.0015 g/L), leucine (0.04 g/L), proline (0.04 g/L) and ampicillin (0.05 g/L) adjusted to pH 7.4. The overnight culture was used to inoculate 22.5 liters of Medium A in a fermentor. The *E. coli* containing the expression vector were grown at 30° C. until the $A_{550}$ reached 7.0 at which time the temperature was raised to 42° C. The cells were harvested 3 hrs after temperature induction at 42° C. by centrifugation and cell pellets divided into 50 g portions prior to freezing at −80° C. until used for preparation of interferon.

PURIFICATION OF Hu-IFN-α001

For purification of Hu-IFN-α001, frozen *E. coli* cell paste was thawed by suspension in 10 volumes of Buffer A (50 mM Tris·HCl, pH 8.0, 50 mM NaCl, 10 mM EDTA, 0.1 mM PMSF, phenylmethylsufonylfluoride). After the addition of egg white lysozyme (0.2 mg/ml) the suspension was sonicated four times with 30 second bursts while kept in an ice bath, then incubated at 23° C. overnight while stirring vigorously to eliminate viscosity contributed by DNA. The suspension was centrifuged for 20 minutes at 12,000 rpm at 4° C. The pellet was resuspended again in 10 volumes of Buffer A with 1% Triton X-100, 50 mM EDTA and 0.5 M NaCl and incubated for at least 2 hours (2–16 hrs) at room temperature with shaking and then centrifuged for 20 min at 12,000 rpm at 4° C. Once again, the pellet was resuspended in 5 volumes of Buffer A with 0.5 M NaCl and incubated for 60 min at room temperature with shaking and then centrifuged for 20 min at 12,000 rpm at 4° C.; the supernatant was discarded. The pellet was dispersed in 2 volumes of Buffer A in the presence of a mixture of oxidized/reduced forms of glutathione (0.2 mM/2.0 mM) and solid guanidine·HCl (2.5 times bacterial weight) was added and the solution was stirred at room temperature for 7 hours. After this, the mixture was diluted tenfold with Buffer A and allowed to stand overnight. Renaturation of the interferon was carried out by very slow addition of Buffer A until the concentration of guinidine·HCl is reduced from 7 M to 0.7 M of The refolding of Hu-IFN-α001 in solution takes more than 15 hours. Since Hu-IFN-α001 contains two disulfide bonds, this step involves slow oxidation of the protein during dilution from guanidine-containing solution. Then suspension was then centrifuged to remove debris. Solid $(NH_4)_2SO_4$ was added to the supernatant to a final concentration 1 M, and the solution, after clarification by centrifugation, was loaded at 5 ml/min onto a column (Pharmacia XK 26 20#18-1000-72) packed with 100 ml of the sorbent Phenyl-Toyopearl 650 S (20–50 μm) (Supelco, #8-14477: 100 g), previously equilibrated with 3–4 column volumes of Buffer B (50 mM Tris·HCl, pH 7.4, 0.5 M guanidine·HCl and 1 M $(NH_4)_2SO_4$. The column effluent was monitored at 280 nm. After loading, the column was washed with Buffer B until the $A_{280}$ of the effluent returned to near baseline level and then was eluted sequentially with 2–3 column volumes of Buffer C (50 mM Tris·HCl, 0.5 M guanidine·HCl, 0.6 M $(NH_4)_2SO_4$) with which the Hu-IFN-α001 was eluted. Peak fractions showing maximum bands of Hu-IFN-α001 on SDS-polyacrylamide gel electrophoresis were pooled. The Phenyl-Toyopearl column was regenerated in situ with 100 ml 0.5 M NaOH and 1 M NaCl solution; and was stored in 0.01% sodium azide. Fractions with Hu-IFN-001 as measured by antiviral activity and/or gel electrophoresis were pooled and concentrated 10-fold with an Amicon Centriprep 10 concentrator. The solution was then diluted 3-fold with Buffer D (20 mM TrisHCl, pH 8.0, 5% glycerol) and was loaded onto a FPLC monoQ HR 10/10 ion exchange column (Pharmacia # 17-0556-01) equilibrated with Buffer D. The column was washed with about 10 ml of Buffer D until the $A_{280}$ reached baseline. Elution of Hu-IFN-α001 was accomplished with a linear gradient of Buffer D and Buffer E (Buffer D plus 1 M NaCl) at a flow rate of 1.5 ml/min from 0 to 100% Buffer E over 3 hours. The Hu-IFN-α001 was eluted at 0.15 M NaCl in a single peak. The fractions were pooled, analyzed by sodium dodecylsulfate (SDS) polyacrylamide gel electrophoresis and assayed for antiviral activity. From 6 g of bacterial pellet (wet weight), about 8–10 mg of purified Hu-IFN-α001 was obtained.

Figure 4:
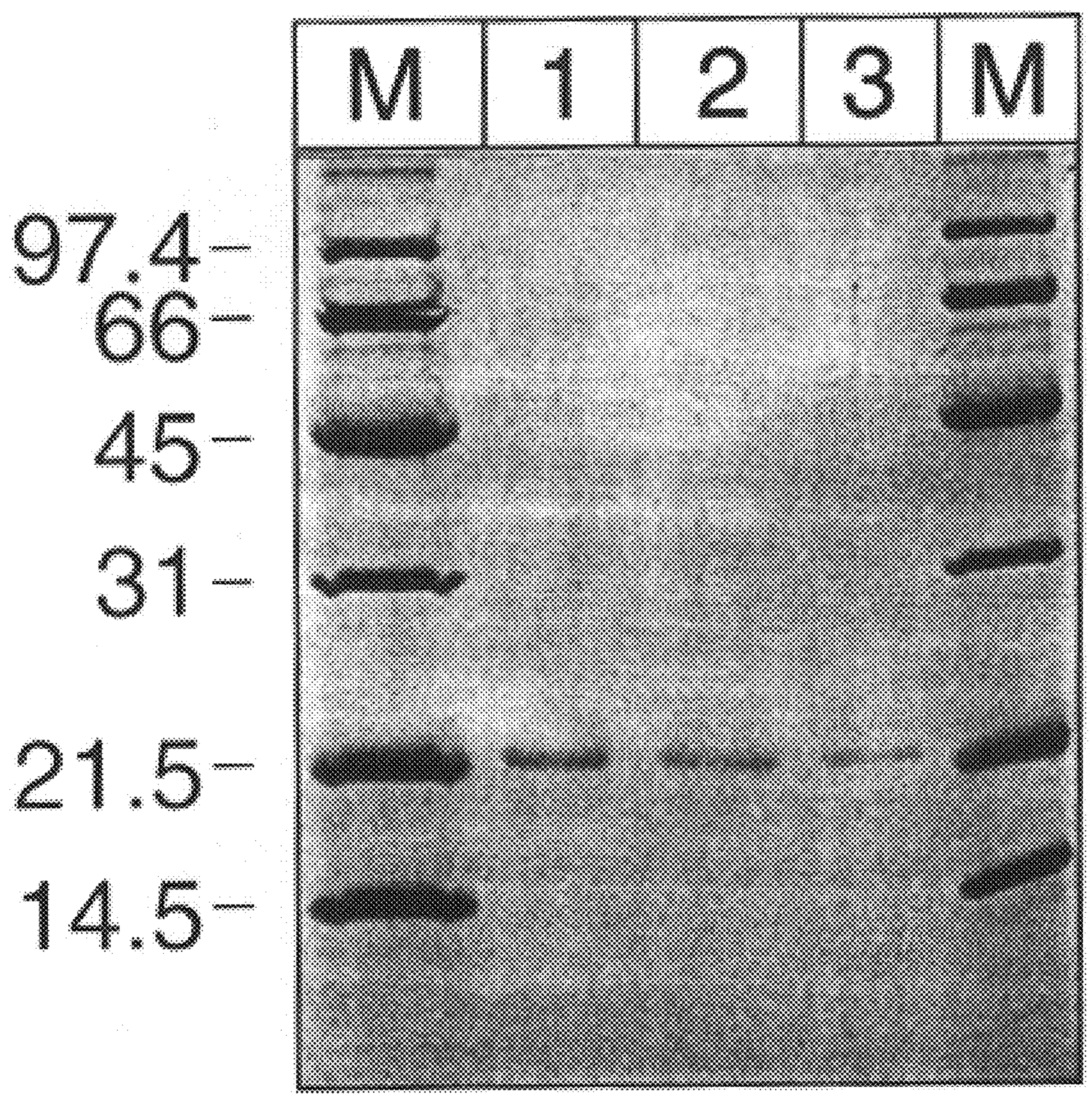
FIG. 4. SDS-Polyacrylamide Gel Electrophoresis of the Purified Hu-IFN-α001. Hu-IFN-α001 was placed in lanes 1, 2 and 3 in amounts of 3 μg, 1.5 μg and 0.75 μg, respectively. The columns labeled M represent the molecular weight markers with the values in kilodaltons given to the left of each respective molecular weight marker.

The purified protein was mixed with 15 μl of SDS sample buffer (0.5 M Tris·HCl, pH 6.8, 1% (v/v) β-mercaptoethanol, 1% (w/v) sodium dodecylsulfate (SDS), 12% (v/v) glycerol, 2 mM ethylenediamineietraacetic acid (EDTA), bromphenol blue) in a total volume of 35 μl. The solution was boiled for two minutes after which 25 μl was loaded onto a 12.5% polyacrylamide gel with a 4% polyacrylamide stacking gel. The separating gel was buffered in 0.3 M Tris·HCl, 0.08% SDS, 2 mM EDTA, pH 8.8. The stacking gel was in 0.065 M TrisHCl, pH 6.8, and 0.05% SDS. The chamber buffer was 25 mM Tris·HCl, 0.1% SDS, 0.2 M glycine. Electrophoresis was carried out for 1 hour at 150 V, 20 mA in the BioRad miniproteian I apparatus (132). The gel was stained with Coomassie Blue R-250 (2.4%. w/v, Coomassie Blue in 45% methanol, 9%, v/v, acetic acid) for 1 hour at room temperature; and destained in 8% acetic acid. From SDS-polyacrylamide gel electrophoresis it was apparent that the purified Hu-IFN-α001 migrated with a $M_r$ of 20,000 as shows in FIG. 4. As indicated in that figure. Hu-IFN-α001 was placed in lanes 1, 2 and 3 in amounts of 3 μg, 1.5 μg and 0.75 μg, respectively. The columns labeled M represent the molecular weight markers with the values in kilodaltons given to the left of each respective molecular weight marker. As can be seen, the Hu-IFN-α001 exhibited a slightly slower mobility than Hu-IFN-αJ on SDS-polyacrylamide gel electrophoresis (SDS PAGE. ref. 132).

Antiviral activity of Hu-IFN-α001 was assayed on bovine MDBK and human FS7 cells with vesicular stomatitis virus (VSV) (Table 5) as described previously (133). The antiviral units were determined with respect to the human IFN-αA international standard Gxa01-901-535. There was approximately equal antiviral activity on human and bovine cells (Table 5) as is seen with many Hu-IFN-α species (17,27, 30,100,103,134).

TABLE 5

| Antiviral Assay of Interferon | | | |
|---|---|---|---|
| | Interferon Titer (units/ml) | | Ratio |
| Sample | FS-7 Cells | MDBK Cells | (FS-7/MDBK) |
| α001 | $1 \times 10^8$ | $1 \times 10^8$ | 1.0 |

The interferon titer is given in units/mg as described (10–12.99, 100, 133, 135) with respect to the international standard for human interferon alpha A Gxa01-901-535 from the National Institutes of Health. Vesicular stomatitis virus (VSV) was used as the challenge virus with human FS-7 and bovine MDBK cells. The ratio of the antiviral activity of the interferon on FS-7 to that on MDBK cells is given in the last column. The samples of Hu-IFN-α001 were prepared as described in the text. Protein was determined by the method of Bradford (136).

Herein has been described an entire new class of molecules designated as super proteins, proteins not present in normal cells, but present in the cells in various diseased states and a method for identifying, producing and expressing such molecules. Although the present embodiment of the invention has been described in detail, it should be understood that various changes, alterations and substitutions can be made therein without departing from the spirit and scope of the invention as defined by the appended claims.

BIBLIOGRAPHY

1. Isaacs, A., and Lindenmann, J., Production of Viral Interfering Substances, U.S. Pat. No. 3,699,222 (Application Ser. No. 757,188) filed Aug. 5, 1968, issued Oct. 17, 1972.

2. Isaacs, A., and Lindenmann, J. (1957) "Virus Interference. I. The interferon," Proc. Royal Society, London Ser. B 147, 258–267.

3. Nagano, Y., and Kojima, Y. (1958) "Inhibition de l'infection vaccinale par un facteur liquide dans le tissu infecté par le virus homologue," C. R. Seances Soc. Biol. Ses Fil. 152, 1627–1629.

4. Wheelock, E. F. (1965) "Interferon-like virus-inhibitor induced human leukocytes by phytohemagglutinin." Science 149, 310–311.

5. Wheelock, E. F. (1966) "Virus replication and high-titered interferon production in human leukocyte cultures inoculated with Newcastle disease virus," *J. Bact.* 92, 1415–1421.

6. Youngner, J. S. and Stinebring, W. R. (1965) "Interferon appearance by endotoxin, bacteria, or viruses in mice pretreated with *Escherichia coli*, endotoxin, or infected with Mycobaclerium tuberculosis," *Nature* 208, 456–458.

7. Youngner. J. S., and Salvin, S. B. (1973) "Production and properties of migration inhibitory factor and interferon in the circulation of mice with delayed hypersensitivity," *J. Immunol* 111, 1914–1922.

8. Cantell, K.. and Tovell, D. R. (1971) "Substitution of milk for serum in the production of human leukocyte interferon," *Appl. Microbiol.* 22. 625–628.

9. Stewart, W. E., II (1979) "The Interferon System." Springer-Verlag, New York, pp. 421.

10. Pestka. S. (1981) "Interferons, Part A," *Methods in Enzymology*, (S. Pestka, ed.) Academic Press, New York, Vol. 78, pp 632.

11. Pestka, S. (1981) "Interferons, Part B," *Methods in Enymology*, (S. Pestka, ed.) Academic Press, New York, Vol. 79, pp 677.

12. Pestka, S. (1986) "Interferons, Part C," Methods in Enzymology, (S. Pestka, ed.) Academic Press, New York, Vol. 119, pp 845.

13. Baron. S., and Dianzani. F. (1977) "The Interferon System: A Current Review to 1978." *Texas Reports on Biology and Medicine* Vol. 35. University of Texas Medical Branch. Galveston, pp. 573.

14. Baron, S., Dianzani, F., and Stanton, G. J. (1982) "The Inerferon System: A Review to 1982 - Part I, " *Texas Reports on Biology and Medicine Vol.* 41, University of Texas Medical Branch, Galveston, pp. 410.

15. Baron, S., Dianzani, F., and Stanton, G. J. (1982) "The Interferon System: A Review to 1982 - Part II, " *Texas Reports on Biology and Medicine Vol.* 41, University of Texas Medical Branch, Galveston, pp. 411–715.

16. Pestka, S., McInnes, J., Havell, E., and Vilcek, J. (1975) "Cell-free Svnthesis of Human Interferon," *Proc. Natl. Acad. Sci. U.S.A.* 72, 3898–3901.

17. Pestka. S. (1983) "The Human Interferons—From Protein Purification and Sequence to Cloning and Expression in Bacteria: Before, Between, and Beyond." *Arch. Biochem. Biophys.* 221, 1–37.

18. Bose. S., Gurari-Rotman, D., Th. Ruegg, U., Corley, K., and C. B. Anfinsen (1976) "Apparent dispensability of the carbohydrate moiety of human interferon for antiviral activity," *J. Biol. Chem.* 251, 1659–1662.

19. Bose. S., and Hickman, J. (1977) "Role of the carbohydrate moiety in determining the survival of interferon in the circulation," *J. Biol. Chem.* 252, 8336–8337.

20. Bridgen, P. J., Anfinsen, C. B., Corley. L., Bose,. S., Zoon, K. C., Th. Ruegg, U., and Buckler, C. E. (1977) "Human lymphoblastoid interferon. Large scale production and partial purification," *J. Biol. Chem.* 252, 6585–6587.

21. Rubinstein, M., Rubinstein, S., Farnilletti, P. C., Gross, M. S., Miller, R. S., Waldman, A. A., and Pestka, S. (1978) "Human Leukocyte Interferon Purified to Homogeneity." *Science* 202, 1289–1290.

22. Rubinstein, M., Rubinstein, S., Familletti, P. C., Miller, R. S., Waldman. A. A., and Pestka, S. (1979) "Human Leukocyte Interferon: Production, Purification to Homogeneity, and Initial Characterization, " *Proc. Natl. Acad. Sci. U.S.A.* 76, 640–644.

23. Rubinstein, M., Rubinstein, S., Familletti. P. C.. Brink, L. D., Hershberg, R. D., Gutterman, J., Hester, J., and Pestka, S. (1979) "Human Leukocyte Interferon Production and Purification to Homogeneity by HPLC, " in *Peptides: Structure and Biological Function* (E. Gross and J. Meienhofer, eds.), Pierce Chemical Company, Rockford, Ill., 99–103.

24. Rubinstein, M., Rubinstein, S., Familletti, P., Gutterman. J., Hester, J., and Pestka, S. (1980) "An Alternative Source of Human Leukocyte Interferon," in *Interferon: Properties and Clinical Uses* (A. Khan, N. O. Hill, and G. L. Dorn, eds.), Leland Fikes Foundation Press, Dallas, Tx. 45–55.

25. Zoon, K. C., Smith, M. E., Bridgen, P. J., zur Nedden, D., and Anfinsen, C. B. (1979) "Purification and partial characterization of human lymphoblastoid interferon," *Proc. Natl Acad. Sci. U.S.A.* 76, 5601–5605.

26. Allen, G., and Fantes, F. H. (1980) "A family of structural genes for human lymphoblastoid (leukocyte-type) interferon," *Nature* (London) 287, 408–411.

27. Rubinstein, M., Levy, W. P., Moscbera, J. A., Lai, C.-Y., Hershberg, R. D., Bartlett, R. T., and Pestka, S. (1981) "Human Leukocyte Interferon: Isolation and Characterization of Several Molecular Forms," *Arch. Biochem. Biophys.* 210. 307–318.

28. Zoon, K. C. (1981) "Purification and Characterization of Human Interferon from Lymphoblastoid (Namalwa) Cultures," *Methods in Enzymology* 78, 457–464.

29. Berg, K., and Heron, I. (1981) "Antibody Affinity Chromatography of Human Leukocyte Interferon, " *Methods in Enzymology* 78, 487–499.

30. Hobbs, D. S., and Pestka, S. (1982) "Purification and Characterization of Interferons from a Continuous Myeloblastic Cell Line, " *J. Biol. Chem.* 257. 4071–4076.

31. Berg, K. (1982) "Purification and characterization of murine and human interferons. A review of the literature of the 1970s," *Acta Path. Microbiol. Immunol. Scand, Section C, Suppl.* 279. 1–136.

32. Pestka, S. (1989) "The Interferons," p. 433–480, in Journal of Chromatography Library—Vol. 43, "Natural Products Isolation" (Edited by G. H. Wagman and R. Cooper) Elsevier, New York, pp 619.

33. Knight, E., Jr. (1976) "Interferon: purification and initial characterization from human diploid cells, " *Proc. Natl. Acad. Sci. U.S.A.* 73, 520–523.

34. Berthold. W.. Tan. C.. and Tan. Y.H. (1978) "Purification and in vitro labeling of interferon from a human fibroblastoid cell line, " *J. Biol. Chem.* 253, 5206–5212.

35. Iwakura, Y., Yonehara, S., and Kawade, Y. (1978) "Purification of mouse L cell interferon. Essentially pure preparations with associated cell growth inhibitory activity," *J. Biol. Chem.* 253, 5074–5079.

36. Kawakita, M., Cabrer, B., Taira, H., Rebello, M., Slattery, E., Weideli, H., and Lengyel. P. (1978) "Purification of interferon from mouse Ehrlich ascites tumor cells," *J. Biol. Chem.* 253, 598–602.

37. De Maeyer-Guignard, J., Tovey, M. G., Gresser, I., and De Maeyer, E. (1978) "Purification of mouse interferon by sequential affinity chromatography on poly(U)—and antibody—agarose columns," *Nature*, London 271, 622–625.

38. Cabrer, B., Taira, H., Broeze, R. J., Kempe, T. D., Williams, K., Slattery, W. H., Konigsberg, W. H., and Lengyel, P. (1979) "Structural characteristics of interferons from mouse Ehrlich ascites tumor cells," *J. Biol. Chem.* 254, 3681–3684.

39. Stein, S., Kenny, C., Friesen, H. J, Shively, J., Del Valle, U., and Pestka, S. (1980) "$NH_2$-Terminal Amino Acid Sequence of Human Fibroblast Interferon," *Proc. Natl. Acad. Sci. U.S.A.* 77, 5716–5719.

40. Friesen, H.-J., Stein, S., Evinger, M., Familletti, P. C., Moschera, J., Meienhofer. J., Shively, J., and Pestka, S. (1981) "Purification and Molecular Characterization of Human Fibroblast Interferon," *Arch. Biochem. Biophys.* 206, 432–450.

41. De Maeyer-Guignard, J. (1981) "Purification of Mouse C-243 Cell Interferon by Affinity Chromatography and Polyacrylamide Gel Electrophoresis," *Methods in Enzymology* 78, 513–522.

42. Okamura, H., Berthold, W., Hood, L., Hunakpiller, M., Inoue, M., Smith-Johannsen, H., and Tan, Y. H. (1981) "Human fibroblastoid interferon: imnnunosorbent column chromatography and N-terminal amino acid sequence," *Biochemisty* 19, 3831–3835.

43. Kawade, Y., Fujisawa, J., Yonehara, S., Iwakura, Y., and Yamamoto, Y. (1981) "Purification of L Cell Interferon," *Methods in Enzymology* 78, 522–535.

44. Knight, E., Jr., and Fahey, D. (1982) "Human Interferon-Beta: Effects of Deglycosylation," *J. Interferon Res.* 2, 421–429.

45. Goeddel, D. V., Shepard, H. M., Yelverton, E., Leung, D., Crea, R., Sloma, A., and Pestka, S. (1980) "Synthesis of Human Fibroblast Interferon by *E. coli,* " *Nucleic Acids Res.* 8, 4057–4074.

46. Taniguchi, T., Ohno, S., Fujii-Kurivama, Y., and Muramatsu, M. (1980) "The nucleotide sequence of human fibroblast interferon cDNA," *Gene,* 10. 11–15.

47. Derynck, R., Content, J., De Clercq, E., Voickaert, G., Tavernier, J., Devos, R., and Fiers, W. (1980) "Isolation and structure of a human fibroblast interferon gene," *Nature* (London) 285, 542–547.

48. Houghton, M., Steward, A. G., Doel, S. W., Emtage, J. S., Eaton, M. A. W., Smith, J. S., Patel, T. P., Lewis, H. M., Porter, A. G., Birch, J. R., Cartwright, T., and Carey, N. H. (1980) "The amino-terminal sequence of human fibroblast interferon as deduced from reverse transcripts obtained using synthetic oligonucleotide primers," *Nucleic Acids Res.* 8, 1913–1931.

49. Friesen, H.-J., and Pestka, S., Preparation of Homogeneous Human Fibroblast Interferon, U.S. Pat. No. 4,289,689 (Application Ser. No. 160.889) filed Jun. 19, 1980, issued Sep. 15, 1981.

50. Pestka, S., and Rubinstein, M., Protein Purification Process and Product, U.S. Pat. No. 4,289,690 (Application Ser. No. 167,165) filed Jul. 9, 1980, issued Sep. 15, 1981.

51. Pestka, S., and Rubinstein, M., Protein Purification Process and Product, U.S. Pat. No. 4,503,035 (Application Ser. No. 465,979) filed Feb. 14, 1983, issued Mar. 5, 1985.

52. Kung, H.-F., Miller, D. L., and Pestka, S., Crystalline Human Leukocyte Interferon, U.S. Pat. No. 4,672,108 (Application Ser. No. 751,753) filed Jul. 3, 1985, issued Jun. 9, 1987.

53. Goeddel, D. V., and Pestka, S., Microbial Production of Mature Human Leukocyte Interferon K and L, U.S. Pat. No.

4,801,685 (Application Ser. No. 56,623), filed Jun. 1, 1987, issued Jan. 31, 1989; European Patent Application 82107337.6.

54. Goeddel, D. V., and Pestka, S., Microbial Production of Mature Human Leukocyte Interferon K and L, U.S. Pat. No. 4,810,645 (Application Ser. No. 822,984) filed Jan. 27, 1986, issued Mar. 7, 1989.

55. Friesen, H.-J., and Pestka. S., Preparation of Homogeneous Human Fibroblast Interferon, U.S. Pat. No. 5,015,730 (Application Ser. No. 386,088), filed Jul. 14, 1989, issued May 14, 1991.

56. Baron, S., Coppenhaver, D. H., Dianzani, F., Fleischmann, W. R., Jr., Hughes, T. K., Jr., Klimpel, G. R., Niesel, D. W., Stanton, G. J., and Tyring, S. K., editors (1992) "Interferon: Principles and Medical Applications," The University of Texas Medical Branch at Galveston, Galvestan, pp. 624.

57. Pestka, S., Langer, J. A., Zoon, K. C., and Samuel, C. E. (1987) "Interferons and Their Actions," *Annu. Rev. Biochem.* 56, 727–777.

58. Havell, E. A., Berman, B., Ogbum, C. A., Berg. K., Paucker, K., and Vilcek, J. (1975) "Two Antigenically Distinct Species of Human Interferon," *Proc. Natl. Acad. Sci. U.S.A* 72, 2185–2187.

59. Cavalieri, R. L., Havell, E. A., Vilcek, J., and Pestka, S. (1977) "Synthesis of Human Interferon by *Xenopus laevis Oocytes*: Two Structural Genes for Interferons in Human Cells," *Proc. Natl. Acad. Sci. U.S.A.* 74, 3287–3291.

60. Familletti, P. C., McCandliss, R., and Pestka, S. (1981) "Production of High Levels of Human Leukocyte Interferon from a Continuous Human Myeloblastoid Cell Culture," *Antimicrob. Agents. Chemother.* 20, 5–9.

61. Pestka, S. (1986) "Interferon from 1981 *to* 1986," , *Methods in Enzymology* (S. Pestka, ed.), Academic Press, New York 119, 3–14.

62. Maeda, S., McCandliss, R., Gross, M., Sloma, P. C., Familletti, J. M., Tabor, M., Evinger, M., Levy, W. P., and Pestka, S. (1981) "Construction and identification of bacterial plasmids containing nucleotide sequence for human leukocyte interferon," *Proc. Natl. Acad. Sci. U.S.A* 77, 7010–7013 (1980); 78, 4648.

63. Goeddel, D. V., and Pestka, S. (1982) Polypeptides, process for their microbial production, intermediates therefor and compositions containing them European Pat. No. Application 81105067.3.

64. Henco, K., Brosius, J., Fujisawa, Fujisawa. J.-I., Haynes, J. R., Hochstadt, J., Kovacic, T., Pasek, M., Schamböck, A., Schmid, J., Todokoro, K., Wälchli, M., Nagata, S., and Weissmann, C. (1985) "Structural Relationship of Human Interferon Alpha Genes and Pseudogenes," *J. Mol. Biol.* 185, 227–260.

65. Diaz, M. O., Pomykala, H., Bohlander, S., Maltepe, E., Olopade, O. (1991) "A Complete Physical Map of the Type-I Interferon Gene Cluster," *J. Interferon Res.*, 11, S85.

66. Owerback, D., Rutter, W. J., Shows, T. B., Gray, P., Goeddel, D. V., and Lawn, R. M. (1981) "Leukocyte and Fibroblast Interferon Genes are Located on Chromosome 9," *Proc. Natl. Acad. Sci. U.S.A.* 78, 3123–3127.

67. Trent, J. M., Olson, S., and Lawn, R. M. (1982) "Chromosomal Localization of Human Leukocyte, Fibroblast and Immune Interferon Genes by Means of in situ Hybridization," *Proc. Natl. Acad. Sci. U.S.A.* 79, 7809–7813.

68. Langer, J. A., and Pestka, S. (1984) "Purification, Bacterial Expression and Biological Activities of the Human Interferons," *J. Invest. Dermatol.* 83, 128–136s.

69. Goeddel, D. V., Yelverton. E., Ullrich, A., Hevneker, H. L., Miozzari, G., Holmes, W., Seeburg, P. H., Dull, T., May, L., Stebbing, N., Crea, R., Maeda, S., McCandliss, A., Sloma, J. M., Tabor, J. M., Gross. M., Familleti, P. C., and Pestka, S. (1981) "Human leukocyte interferon produced in *E. coli* is biologically active," *Nature* 287, 411–416.

70. Streuli. M., Nagata, S., and Weissmann, C. (1980) "At Least Three Human Type α Interferons: Structure of α2," *Science* 209, 1343–1347.

71. Lawn, R. M., Gross, M., Houk, C. M., Franke, A. E., Gray, P. V., and Goeddel, D. V. (1981) "DNA Sequence of a Major Human Leukocyte Interferon Gene," *Proc. Natl. Acad. Sci. U.S.A.* 78, 5435–5439.

72. Dworkin-Rastl, E., Dworkin, M. B., and Swetly, P. (1982) "Molecular cloning of human alpha and beta interferon genes from Namalwa cells," *J. Interferon Research* 2, 575–585.

73. Physicians' Desk Reference, PDR, 47th Edition, 1993: pages 1078–1079; 1879–1881; 2006–2008; 2194–2201.

74. Dianzani, F. (1992) Biological Basis for Therapy and for Side Effects in "Interferon: Principles and Medical Applications," (Baron, S., Coppenhaver, D. H., Dianzani, F., Fleischmann, W. R., Jr., Hughes, T. K., Jr., Klimpel, G. R., Niesel, D. W., Stanton, G. J., and Tyring, S. K., editors) The University of Texas Medical Branch at Galveston, Galvestan, 409–416.

75. Hosoi, H., Mivaki, K., and Yamanaka, M. (1992) "The Interferon α2 Gene in Japanese Patients with Chronic Viral Hepatitis Who Developed Antibodies After Recombinant Interferon α2A Treatment," *International Society for Study of the Liver*, Brighton, UK. Jun. 3–6th, 1992; p 113, Abstract.

76. Desai, M., Hussain, M., Lee, N., Ni, D., Liao, M.-J., and Testa, D. (1992) "Identification of IFN-α2 Transcripts in Sendai Virus Induced Human Leukocytes by PCR," *J. Interferon Res.* 12, S138.

77. Adolf, G. R., Kalsner. I., Ahorn, H., Maurer-Fogy, I., and Cantell, K. (1991) "Natural Human Interferon Alpha-2 is O-glycosylated," *Biochem. J.* 276, 511–518.

78. Zoon, K. C., Miller, D., Bekisz, J., zur Nedden, D., Ny, J. C., Nguyen, N. Y., and Hu, R. (1992) "Purification and Characterization of Multiple Components of Human Lymphoblastoid Interferon-α," *J. Biol. Chem.* 267, 15210–15216.

79. Emanuel, S. L., and Pestka, S. (1993) "Human interferon-αA, -α2 and -α2(Arg) Genes in Genomic DNA," *J. Biol. Chem.* 268, 12565–12569.

80. Koeffler, H. P. and Golde, D. W. (1978) "Acute Myelogenous Leukemia: A Human Cell Line Responsive to Colony-Stimulating Activity," *Science* 200, 1153–1154.

81. Nadkarni. J. S., Nadkarni, J. J., Clifford, P., Manolov, G., Fenyo, E. M., and Klein, E. (1969) "Characteristics of new cell lines derived from Burkitts lymphomas," *Cancer* 23, 64–79.

82. Beaucage, S. L., and Carothers, M. H. (1981) "Deoxynucleoside Phosphoramidites-A New Class of Key Intermediates for Deoxypolynucleotide Synthesis," *Tetrahedron Lett.* 22, 1859–1862.

83. Chow, R., Kempe, T., and Palm, G. (1981) "Synthesis of Oligodeoxyribonucleotides on Silica Gel Support," *Nucleic Acids Res.* 9, 2807–2817.

84. Johnson, B. A., Mc Clain, S. G., and Doran, E. R. (1990) "Rapid Purification of Synthetic Oligonucleotides: A Convenient Alternative to High-Performance Liquid Chromatography and Polyacrylamide Gel Electrophoresis," *Biotecniques* 8, 424–429.

85. Alting-Mees, M. A. and Short, J. M. (1989) "pBluescript II: gene mappig vectors," *Nucelic Acids Res.* 17, 9494.

86. Sambrook, J., Frisch, E. F., and Maniatis, T. (1989). *Molecular Cloning: A Laboratory Manual.* Three Volume Set, Cold Spring Harbor Laboratory, New York.

87. Binboim, H. C., and Doly, J. (1979) "A Rapid Alkaline Extraction Procedure for Screening Recombinant Plasmid DNA," *Nucleic Acis Res.* 7, 1513–1523.

88. Sangyer. F., Nicklen, S., and Coulson, A. R. (1977) "DNA Sequencing with Chain Terminating Inhibitors," *Proc. Natl. Acad. Sci. U.S.A.* 74, 5463–5467.

89. Tabor, S., and Richardson, C. C. (1987) "DNA Sequence Analysis with a Modified Bacteriophage T7 DNA Polymerase," *Proc. Natl. Acad. Sci. U.S.A.* 84, 4767–4771.

90. Kawasaki, E. S. and Wang, A. M. (1989) "Detecion of Gene Expression," In: *PCR Technology: Principles and Applications of DNA Amplification.* (Erlich, H. A. ed.) Stockton Press, Inc., New York, Ny., pp 89–97.

91. McCandliss, R. Sloma, A., and Pestka, S. (1981) "Isolation and Cell-free Translation of Human Interferon mRNA from Fibroblasts and Leukocytes," in *Methods in Enzymology,* Vol. 79 (S. Pestka, ed.), Academic Press, New York, 51–59.

92. Chomczynski, P., and Sacchi, N. (1 987) "Single Step Method of RNA Isolation by Acid Guanidinium Thiocyanate-Phenol-Chlorofonn Extraction," *Anal. Bioch.* 162, 156–159.

93. Pellicer, A., Wigler, M., and Axel, R. (1978) "The Transfer and Stable Integration of the HSV Thymidine Kinase Gene into Mouse Cells," *Cell* 14, 133–14.

94. Gross-Bellard, M., Oudet, P., and Chambon, P. (1973) "Isolation of High-Molecular-Weight DNA from Mammalian Cells," *Eur. J. Biochem.* 36, 32–38.

95. Saiki, R. K., Scharf, S., Faloona, F., Mullis, K. B., Hom, G. T., Erlich, H. A., and Arnheim, N. (1985) "Enzymatic Amplification of Beta-Globin Genomic Sequences and Restriction Site Analysis for Diagnosis of Sickle Cell Anemia," *Science* 230, 1350–1354.

96. Keohavong, P., and Thilly, W. G. (1989) "Fidelity of DNA PStymerases in DNA Amplification," *Proc. Natl. Acad. Sci. U.S.A.* 86, 9253–9257.

97. Hotta, K., Collier, K. J. and Pestka, S. (1986) "Detection of a Single Base Substitution Between Human Leukocyte Interferon αA and α2 Genes with Octadecyl Deoxyoligonucleotide Probes," in *Method in Enzymology* (S. Peska, ed.), Academic Press, New York 119, 481–485.

98. Hotta, K., Monahan, J., Collier, K. J., and Pestka, S. (1988) "Detection of Hunan Leukocyte Interferon αA and α2 Genes in Genomic DNAs by the Use of Deoxyoctadecyloligonucleotide Probes," *J. Interferon Res.* 8, 51–60.

99. Pestka, S., and Baron, S. (1981) "Definition and Classification of the Interferons," in *Methods in Enzymology* (S. Pestka, ed.), Academic Press, New York, 78, 3–14.

100. Pestka, S. (1986) "Interferon Standards and General Abbreviations," in *Methods in Enzymology* (S. Pestka, ed.), Academic Press. New York, 119, 14–23.

101. Evinger, M., Maeda, S., and Pestka, S. (1981) "Recombinant Human Leukocyte Interferon Produced in Bacteria Has Antiproliferative Activity," *J. Biol. Chem.* 256, 2113–2114.

102. Herberman, R. B., Ortaldo, J. R., Mantovani, A., Hobbs, D. S., Kung, H.-F., and Pestka, S. (1982) "Effect of Human Recombinant Interferon on Cytotoxic Activitv of Natural Killer (NK) Cells and Monocytes," *Cell Immunol.* 67, 160–167.

103. Rehberg, E., Kelder, B., Hoal, E. G., and Pestka, S. (1982) "Specific Molecular Activities of Recombinant and Hybrid Leukocyte Interferons," *J. Biol. Chem.* 257., 11497–11502.

104. Jones, C.M, Varesio, L., Herberman, R. B., and Pestka, S. (1982) "Interferon Activates Macrophages to Produce Plasminogen Activator," *J. Interferon Res.* 2, 377–386.

105. Grant, S., Bhalla, K., Weinstein, I. B., Pestka, S., and Fisher, P. B (1982) "Differential Effect of Recombinant Human Leukocyte Interferon on Human Leukemic and Normal Myeloid Progenitor Cells," *Biochem. Biophys. Res. Commun.* 108, 1048–1055.

106. Ortaldo, J. R., Herberman, R. B., and Pestka. S. (1982) "Augmentation of Human Natural Killer Cells with Human Leukocyte and Human Recombinant Leukocyte Interferon," in *NK Cells and Other Natural Effector Cells* (R. B. Herberman, ed.), Academic Press, New York, 1279–1283.

107. Ortaldo, J. R., Mason. A., Rehberg, E., Moschera, J., Kelder, B., Pestka, S., and Herberman, R. B. (1983) "Effects of Recombinant and Hybrid Recombinant Human Leukocyte Interferons on Cytotoxic Activity of Natural Killer Cells," *J. Biol. Chem.* 258, 15011–15015.

108. Fisher, P., Miranda, A. F., Babiss, L. E., Pestka, S., and Weinstein, I. B. (1983) "Opposing Effects of Interferon Produced in Bacteria and of Tumor Promoters on Myogenesis in Human Myoblast Cultures," *Proc. Natl. Acad. Sci. U.S.A.* 80, 2961–2965.

109. Sen, G. C., Herz, R. E., Davatelis, V., and Pestka. S. (1984) "Antiviral and Protein-Inducing Activities of Recombinant Human Leukoclte Interferons and Their Hybrids," *J. Virol.* 50, 445–450.

110. Giacomini, P., Aguzzi, A., Pestka, S., Fisher, P. B., and Ferrone, S. (1984) "Modulation by Recombinant DNA Leukocyte (α) and Fibroblast (β) Interferons of the Expression and Shedding of HLA and Tumor Associated Antigens by Melanoma Cells," *J. Immunol.* 133, 1649–1655.

111. Greiner, J. W., Hand, P. H., Noguchi, P., Fisher, P. B., Pestka, S., and Schlom, J. (1984) "Enhanced Expression of Surface Tumor-Associated Antigens on Human Breast and Colon Tumor Cells After Recombinant Human Leukocyte α-Interferon Treatment," *Cancer Res.* 44, 3208–3214.

112. Fisher, P. B., Prignoli, D. R., Hermo, H., Jr., Weinstein. I. B., and Pestka. S. (1985) "Effects of Combined Treatment with Interferon and Mezerein on Melanogenesis and Grouth in Human Melanoma Cells," *J. Interferon Res.* 5, 11–22.

113. Grant, S., Bhalla, K., Weinstein, I. B., Pestka, S., Mileno, M. D., and Fisher, P. B. (1985) "Recombinant Human Interferon Sensitizes Resistant Myeloid Leukemic Cells to Induction of Terminal Differentiation," *Biochem. Biophys. Res. Commun.* 130, 379–388.

114. Guadagni, F., Schlom, J., Johnston, W. W., Szpak, C. Z., Goldstein, D., Smalley, R., Simpson, J. F., Borden, E. C., Pestka, S., and Greiner, J. W.,. (1989) "Selective Interferon-Induced Enhancement of Tumor-Associated Antigens on a Spectrum of Freshly Isolated Human Adenocarcinoma Cells," *J. Natl. Cancer Inst.* 81, 502–512.

115. Sperber, S. J., Gocke, D. J., Haberzettl, C., Kuk, R., Schwvartz, B., and Pestka, S. (1992) "Anti-HIV-1 Activity of Recombinant and Hybrid Species of Interferon Alpha," *J. Interferon Res.* 12, 363–368.

116. Huber, C., Flener, R., and Gastl, G. (1985) "Interferon-Alpha-2c in the Treatment of Advanced Hairy Cell Leukemia," *Oncology* 42, Suppl 1, 7–9.

117. Foon, K. A., Maluish, A. E., Abrams, P. G., Wrightington, S., Stevenson, H. C., Alarif, A., Fer, M. F., Overton, W. R., and Poole, M. (1986) "Recombinant Leukocyte A Interferon Therapy for Advanced Hairy Cell Leukemia" *Am. J. Med.* 80, 351–356.

118. Steis, R. G., Smith, J. W. II, Urba, W. J., Clark, J. W., Itri, L. M., Evans, L. M., Schoenberge, C., and Longo, D. L. (1988) "Resistance to Recombinant Interferon Alfa-2 in Hairy Cell Leukemia Associated with Neutralizing Anti-interferon Antibodies," *New Engl. J. Med.* 318, 1409–1413.

119. Von Wussow, P., Freund, M., Hartmann, F., Diedrich, H., Poliwoda, H., and Deicher, H. (1987) "Anti Interferon Antibodies: Phannokinetics and Clinical Significance," *J. Interferon Res.* 7, 680.

120. Freund, M., on Wussow, P., Diedrich, H., Eisert, R., Link, H., Wilke, H., Buchholz, F., LeBlanc, S., Fonatsch, C., Deicher, H., and Poliwoda, H. (1989) "Recombinant Human Interteron (IFN) Alpha-2b in Chronic Myelogenous Leukemia: Dose Dependency of Response and Frequency of Neutralizing Anti-Interferon Antibodies," *Br. J. Haemato.* 72, 350–356.

121. Itri, L. M., Campion, M., Dennin, R. A., Palleroni, A. V., Gutterman, J. O., Groopman, J. E., and Trown, P. W. (1987) "Incidence and Clinical Significance of Neutralizing Antibodies in Patients Receiving Recombinant Interferon Alpha-1A by Intramuscular Injection," *Cancer* 59, 668–674.

122. Moormeier, J. A., Westbrook, C. A., Ratain, M. J., and Golomb, H. M. (1989) "Interferon Alfa-2b Antibodies and Clinical Resistance in a Patient with Hairy Cell Leukemia," *Leuk. Lymphoma* 1, 43–45.

123. Quesada, J. R., Rios, A., Swanson, D. A., Trowm, P., and Gutterman, J. U. (1985) "Antitumor Activity of Recombinant-derived Interferon Alpha in Metastatic Renal Cell Carcinoma," *J. Clin. Oncol.* 3, 1522–1528.

124. Antonelli, G., Currenti, M., Turriziani, O., and Dianzani, F. (1991) "Neutralizing Antibodies to Interferon α: Relative Frequency in Patients Treated with Different Interferon Preparations," *J. Infect. Dis.* 163, 882–885.

125. Colamonici, O., Porterfield, B., and Diaz, M. O. (1991) "Interferon Sensitivity of Human Leukemia Cell Lines With and Without Deletion of the Interferon Genes," *J. Interferon Res.* 11, S54.

126. Grander, D., Heyman, M., Bröndum-Nielsen, K., Liu, Y., Lundgren, E., Söderhäll, S., and Einhom, S. (1992) "Interferon System in Primary Acute Lymphocytic Leukemia Cells With or Without Deletions of the α-/β-Interferon Genes," *Blood* 79, 2076–2083.

127. Nishimura, A., Morita, M., Nishimura, Y. and Sugino, Y. (1990) "A Rapid and Highly Efficient Method for Preparation of Competent *Escherichia coli* Cells ," *Nucleic Acids Research* 18, 6169.

128. Lee, S. and Rashid, S. (1990) "A Simple Procedure for Maximum Yield of High-quality Plasmid DNA," *BioTechniques* 9, 676–679.

129. Mashko, S. V., Veiko, V. P., Lapidus, A. L., Lebedeva, M. I., Mochculsky, A. V., Shechter, I.I., Trukhan, M. E., Ratmanova, K.I., Rebentish, B. A., Kaluzhsky, V. E. and Debabov, V. G. (1990) TGATG vector: a new expression system for cloned foreign genes in *Escherichia coli* cells. *Gene* 88, 121–126.

130. Caruthers, M. H., Barone, A. D., Beaucage, S. L., Dodds, D. R., Fisher, E. F., McBride, L. J., Matteucci, M., Stabinsky, Z., Tang, I. Y. (1987) "Chemical Synthesis of Deoxyoligonucleotides by the Phosphoramidite Method," *Methods in Enzymology* 154, 287–313.

131. Wang, P., Izoto L., Mariano, T. M., Donnelly, R. and Pestka, S. (1994) "Construction and Activity of Phosphorylatable Human Interferon-αB2 and Interferon-αA/D." *J. Interferon Res.* 14, 41–46.

132. Laemnili, U. K. (1990) Cleavage of structural proteins during the assembly of the head of bacteriophage T4. *Nature* (London) 227: 680–685.

133. Familletti, P. C., Rubinstein, S., and Pestka, S. (1981) "A Convenient and Rapid Cytopathic Effect Inhibition Assay for Interferon," in *Methods in Enzymology,* Vol. 78 (S. Pestka, ed.), Academic Press, New York, 387–394.

134. Staehelin, T., Hobbs, D. S., Kung, H.-F., Lai, C.-Y., and Pestka, S. (1981) "Purification and Characterization of Recombinant Human Leukocyte Interferon (IFLrA) with Monoclonal Antibodies," *J. Biol. Chem.* 256, 9750–9754.

135. Pestka. S. (1981) "Standard Media and General Abbreviations," in *Methods in Enzymology,* Vol. 78 (S. Pestka, ed.), Academic Press, New York, 22–25.

136. Bradford, M. M. (1976) "A Rapid and Sensitive Method for the quantitation of Microgram quantities of Protein Utilizing the Principle of Protein-dye Binding," *Anal. Biochem.* 72, 248–254.

I claim the following:

1. A purified or recombinantly produced polypeptide comprising an amino acid sequence of a mutant human interferon alpha (IFNα) encoded by a gene from a diseased cell, which amino acid sequence is different by one to six amino acid residues from the naturally occurring form of the human IFNα.

2. The polypeptide of claim 1, which exhibits at least one of antiviral activity, antitumor activity, growth inhibition activity and immunosupressive activity at interferon titers of $10^8$ units/ml.

3. The polypeptide of claim 1, which polypeptide is purified to homogeneity.

4. A purified or recombinantly produced polypeptide comprising an amino acid sequence of mutant interferon which is encoded by a gene from a diseased cell, which interferon amino acid sequence differs from normal alleles of interferon genes by one to six amino acid residues, wherein the mutant interferon amino acid sequence is encoded by a gene which hybridizes under stringent wash conditions of 6×SSC at 0° C. to a normal human interferon gene.

5. The polypeptide of claim 4, wherein the normal human interferon gene is selected from the group consisting of Hu-IFN-α, Hu-IFN-β, Hu-IFN-γ and Hu-IFN-ω.

6. The polypeptide of claim 4, which exhibits at least one of antiviral activity, antitumor activity, growth inhibition activity and immunosupressive activity at interferon titers of $10^8$ units/ml.

7. The polypeptide of claim 4, which polypeptide is purified to homogeneity.

8. A purified preparation of a mutant human interferon protein which is encoded by a gene from a diseased human cell, which mutant interferon has an amino acid sequence that (i) differs from norml human interferon Hu-IFN-α, Hu-IFN-β, Hu-IFN-γ and Hu-IFN-ω genes by one to six amino acid residues, and (ii) which mutant interferon is encoded a nucleotide sequence which hybridizes under stringent wash conditions of 6×SSC at 0° C. to a human Hu-IFN-α, Hu-IFN-β, Hu-IFN-γ or Hu-IFN-ω gene.

9. The polypeptide of claim 8, which mutant interferon exhibits at least one of antiviral activity, antitumor activity, growth inhibition activity and immunosupressive activity at interferon titers of $10^8$ units/ml.

10. A purified preparation of a mutant human interferon protein which is encoded by a gene from a diseased human cell, which interferon has an amino acid sequence that differs by up to 5 amino acid residues from normal human interferon Hu-IFNα, Hu-IFN-β, Hu-IFN-γ or Hu-IFN-ω protein.

11. The polypeptide of claim 10, which interferon exhibits at least one of antiviral activity, antitumor activity, growth inhibition activity and immunosupressive activity at interferon titers of $10^8$ units/ml.

* * * * *

UNITED STATES PATENT AND TRADEMARK OFFICE

CERTIFICATE OF CORRECTION

PATENT NO. : 6,300,474 B1
DATED : October 9, 2001
INVENTOR(S) : Sidney Pestka

It is certified that error appears in the above-identified patent and that said Letters Patent is hereby corrected as shown below:

Column 31,
Lines 51 and 66, change "immunosupressive" to -- immunosuppressive --.
Lines 52 and 67, change "ml" to -- mg --.

Column 32,
Lines 55 and 65, change "immunosupressive" to -- immunosuppressive --.
Lines 56 and 66, change "ml" to -- mg --.

Signed and Sealed this

Nineteenth Day of July, 2005

JON W. DUDAS
*Director of the United States Patent and Trademark Office*

SEQUENCE LISTING

```
(1) GENERAL INFORMATION:

   (iii) NUMBER OF SEQUENCES: 16


(2) INFORMATION FOR SEQ ID NO:1:

     (i) SEQUENCE CHARACTERISTICS:
          (A) LENGTH: 570 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO

    (iv) ANTI-SENSE: NO

    (vi) ORIGINAL SOURCE:
          (A) ORGANISM: Homo sapiens

    (ix) FEATURE:
          (A) NAME/KEY: CDS
          (B) LOCATION: 1..570

    (xi) SEQUENCE DESCRIPTION: SEQ ID NO:1:
```

-continued

```
ATG GCC TTG TCC TTT TCT TTA CTG ATG GTC GTG CTG GTA CTC AGC TAC        48
Met Ala Leu Ser Phe Ser Leu Leu Met Val Val Leu Val Leu Ser Tyr
  1               5                  10                  15

AAA TCC ATC TGC TCT CTG GGC TGT GAT CTG CCT CAG ACC CAC AGC CTG        96
Lys Ser Ile Cys Ser Leu Gly Cys Asp Leu Pro Gln Thr His Ser Leu
             20                  25                  30

CGT AAT AGG AGG GCC TTG ATA CTC CTG GCA CAA ATG GGA AGA ATC TCT       144
Arg Asn Arg Arg Ala Leu Ile Leu Leu Ala Gln Met Gly Arg Ile Ser
         35                  40                  45

CCT TTC TCC TGC TTG AAG GAC AGA CAT GAA TTC AGA TTC CCA GAG GAG       192
Pro Phe Ser Cys Leu Lys Asp Arg His Glu Phe Arg Phe Pro Glu Glu
     50                  55                  60

GAG TTT GAT GGC CAC CAG TTC CAG AAG ACT CAA GCC ATC TCT GTC CTC       240
Glu Phe Asp Gly His Gln Phe Gln Lys Thr Gln Ala Ile Ser Val Leu
 65                  70                  75                  80

CAT GAG ATG ATC CAG CAG ACC TTC AAT CTC TTC AGC ACA GAG GAC TCA       288
His Glu Met Ile Gln Gln Thr Phe Asn Leu Phe Ser Thr Glu Asp Ser
                 85                  90                  95

TCT GCT GCT TGG GAA CAG AGC CTC CTA GAA AAA TTT TCC ACT GAA CTT       336
Ser Ala Ala Trp Glu Gln Ser Leu Leu Glu Lys Phe Ser Thr Glu Leu
            100                 105                 110

TAC CAG CAA CTG AAT GAC CTG GAA GCA TGT GTG ATA CAG GAG GTT GGG       384
Tyr Gln Gln Leu Asn Asp Leu Glu Ala Cys Val Ile Gln Glu Val Gly
        115                 120                 125

GTG GAA GAG ACT CCC CTG ATG AAT GAG GAC TCC ATC CTG GCT GTG AGG       432
Val Glu Glu Thr Pro Leu Met Asn Glu Asp Ser Ile Leu Ala Val Arg
    130                 135                 140

AAA TAC TTC CAA AGA ATC ACT CTT TAT CTA ACA GAG AAG AAA TAC AGC       480
Lys Tyr Phe Gln Arg Ile Thr Leu Tyr Leu Thr Glu Lys Lys Tyr Ser
145                 150                 155                 160

CCT TGT GCC TGG GAG GTT GTC AGA GCA GAA ATC ATG AGA TCC CTC TCG       528
Pro Cys Ala Trp Glu Val Val Arg Ala Glu Ile Met Arg Ser Leu Ser
                165                 170                 175

TTT TCA ACA AAC TTG CAA AAA AGA TTA AGG AGG AAG GAT TGA               570
Phe Ser Thr Asn Leu Gln Lys Arg Leu Arg Arg Lys Asp
            180                 185                 190
```

(2) INFORMATION FOR SEQ ID NO:2:

(i) SEQUENCE CHARACTERISTICS:
(A) LENGTH: 189 amino acids
(B) TYPE: amino acid
(D) TOPOLOGY: linear (ii) MOLECULE TYPE: protein (xi) SEQUENCE DESCRIPTION: SEQ ID NO:2:

```
Met Ala Leu Ser Phe Ser Leu Leu Met Val Val Leu Val Leu Ser Tyr
  1               5                  10                  15

Lys Ser Ile Cys Ser Leu Gly Cys Asp Leu Pro Gln Thr His Ser Leu
             20                  25                  30

Arg Asn Arg Arg Ala Leu Ile Leu Leu Ala Gln Met Gly Arg Ile Ser
         35                  40                  45

Pro Phe Ser Cys Leu Lys Asp Arg His Glu Phe Arg Phe Pro Glu Glu
     50                  55                  60

Glu Phe Asp Gly His Gln Phe Gln Lys Thr Gln Ala Ile Ser Val Leu
 65                  70                  75                  80

His Glu Met Ile Gln Gln Thr Phe Asn Leu Phe Ser Thr Glu Asp Ser
                 85                  90                  95

Ser Ala Ala Trp Glu Gln Ser Leu Leu Glu Lys Phe Ser Thr Glu Leu
```

```
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185
```

(2) INFORMATION FOR SEQ ID NO:3:

(i) SEQUENCE CHARACTERISTICS:
 (A) LENGTH: 189 amino acids
 (B) TYPE: amino acid
 (C) STRANDEDNESS: single
 (D) TOPOLOGY: linear (ii) MOLECULE TYPE: protein (iii) HYPOTHETICAL: NO (iv) ANTI-SENSE: NO (vi) ORIGINAL SOURCE:
 (A) ORGANISM: Homo sapiens (xi) SEQUENCE DESCRIPTION: SEQ ID NO:3:

```
Met Ala Arg Ser Phe Ser Leu Leu Met Val Val Leu Val Leu Ser Tyr
1               5                   10                  15

Lys Ser Ile Cys Ser Leu Gly Cys Asp Leu Pro Gln Thr His Ser Leu
            20                  25                  30

Arg Asn Arg Arg Ala Leu Ile Leu Leu Ala Gln Met Gly Arg Ile Ser
        35                  40                  45

Pro Phe Ser Cys Leu Lys Asp Arg His Glu Phe Arg Phe Pro Glu Glu
    50                  55                  60

Glu Phe Asp Gly His Gln Phe Gln Lys Thr Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Phe Ile Leu Ala Val Arg
    130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Asn Leu Lys Lys Gly Leu Arg Arg Lys Asp
            180                 185
```

(2) INFORMATION FOR SEQ ID NO:4:

(i) SEQUENCE CHARACTERISTICS:
 (A) LENGTH: 18 base pairs
 (B) TYPE: nucleic acid (C) STRANDEDNESS: single
(D) TOPOLOGY: linear (ii) MOLECULE TYPE: DNA
(A) DESCRIPTION: Primer I (iii) HYPOTHETICAL: NO (iv) ANTI-SENSE: NO (xi) SEQUENCE DESCRIPTION: SEQ ID NO:4:

TGGGCTGTGA TCTGCCTC 18

(2) INFORMATION FOR SEQ ID NO:5:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA
(A) DESCRIPTION: Primer II (iii) HYPOTHETICAL: NO (iv) ANTI-SENSE: NO (xi) SEQUENCE DESCRIPTION: SEQ ID NO:5:

CATGATTTCT GCTCTGACAA CC 22

(2) INFORMATION FOR SEQ ID NO:6:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA
(A) DESCRIPTION: Primer III (iii) HYPOTHETICAL: NO (iv) ANTI-SENSE: NO (xi) SEQUENCE DESCRIPTION: SEQ ID NO:6:

AACCCACAGC CTGGGTAG 18

(2) INFORMATION FOR SEQ ID NO:7:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:7:

GCGGGCCCCA ATGGCCYTGY CCTTT 25

(2) INFORMATION FOR SEQ ID NO:8:

(i) SEQUENCE CHARACTERISTICS:
(A) LENGTH: 24 base pairs
(B) TYPE: nucleic acid (C) STRANDEDNESS: single
(D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:8:

GCTCTAGAAY TCATGAAAGY GTGA 24

(2) INFORMATION FOR SEQ ID NO:9:

(i) SEQUENCE CHARACTERISTICS:
(A) LENGTH: 9 base pairs
(B) TYPE: nucleic acid
(C) STRANDEDNESS: single
(D) TOPOLOGY: linear (ii) MOLECULE TYPE: DNA
(A) DESCRIPTION: AlwNI restriction endonuclease recognition site used to splice the Hu-IFN-′001 wherein N represents any nucleotide (iii) HYPOTHETICAL: NO (iv) ANTI-SENSE: NO (xi) SEQUENCE DESCRIPTION: SEQ ID NO:9:

CAGNNNCTG 9

(2) INFORMATION FOR SEQ ID NO:10:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA
(A) DESCRIPTION: Primer used in sequencing of Hu-IFN-′

(iii) HYPOTHETICAL: NO (iv) ANTI-SENSE: NO (xi) SEQUENCE DESCRIPTION: SEQ ID NO:10:

CTTGAAGGAC AGACATG 17

(2) INFORMATION FOR SEQ ID NO:11:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA
(A) DESCRIPTION: Primer used in sequencing of Hu-IFN-′

(iii) HYPOTHETICAL: NO (iv) ANTI-SENSE: NO (xi) SEQUENCE DESCRIPTION: SEQ ID NO:11:

CTGTCCTCCA TGAGATG 17

(2) INFORMATION FOR SEQ ID NO:12:

(i) SEQUENCE CHARACTERISTICS:

(A) LENGTH: 17 base pairs
(B) TYPE: nucleic acid
(C) STRANDEDNESS: single
(D) TOPOLOGY: linear (ii) MOLECULE TYPE: DNA
(A) DESCRIPTION: Primer used in sequencing of Hu-IFN-'

(iii) HYPOTHETICAL: NO (iv) ANTI-SENSE: NO (xi) SEQUENCE DESCRIPTION: SEQ ID NO:12:

GGTCATTCAG CTGCTGG 17

(2) INFORMATION FOR SEQ ID NO:13:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA
(A) DESCRIPTION: Primer used in sequencing of Hu-IFN-'

(iii) HYPOTHETICAL: NO (iv) ANTI-SENSE: NO (xi) SEQUENCE DESCRIPTION: SEQ ID NO:13:

TCCTCCTTCA TCAGGGG 17

(2) INFORMATION FOR SEQ ID NO:14:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA
(A) DESCRIPTION: Primer used in sequencing of Hu-IFN-'

(iii) HYPOTHETICAL: NO (iv) ANTI-SENSE: NO (xi) SEQUENCE DESCRIPTION: SEQ ID NO:14:

ATTAACCCTC ACTAAAG 17

(2) INFORMATION FOR SEQ ID NO:15:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA
(A) DESCRIPTION: Primer used in sequencing of Hu-IFN-'

(iii) HYPOTHETICAL: NO (iv) ANTI-SENSE: NO (xi) SEQUENCE DESCRIPTION: SEQ ID NO:15:

TAATACGACT CACTATA 17

(2) INFORMATION FOR SEQ ID NO:16:

-continued

```
     (i) SEQUENCE CHARACTERISTICS:
          (A) LENGTH: 166 amino acids
          (B) TYPE: amino acid
          (D) TOPOLOGY: unknown

    (ii) MOLECULE TYPE: protein

   (iii) HYPOTHETICAL: NO

   (vii) IMMEDIATE SOURCE:
          (B) CLONE: Hu-IFN-alpha001

    (xi) SEQUENCE DESCRIPTION: SEQ ID NO:16:

Cys Asp Leu Pro Gln Thr His Ser Leu Arg Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Glu Phe Arg Phe Pro Glu Glu Glu Phe Asp Gly His Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165
```